(12) United States Patent
Titus et al.

(10) Patent No.: US 10,527,544 B2
(45) Date of Patent: Jan. 7, 2020

(54) ATR-FTIR FOR NON-INVASIVE DETECTION OF COLITIS

(71) Applicants: GEORGIA STATE UNIVERSITY RESEARCH FOUNDATION, INC., Atlanta, GA (US); THE UNITED STATES GOVERNMENT AS REPRESENTED BY THE DEPARTMENT OF VETERANS AFFAIRS, Washington, DC (US)

(72) Inventors: Jitto Titus, Acworth, GA (US); Emilie Viennois, Atlanta, GA (US); A. G. Unil Perera, Mableton, GA (US); Merlin Didier, Decatur, GA (US)

(73) Assignees: GEORGIA STATE UNIVERSITY RESEARCH FOUNDATION, INC., Atlanta, GA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 15/735,661

(22) PCT Filed: Jun. 13, 2016

(86) PCT No.: PCT/US2016/037172
§ 371 (c)(1),
(2) Date: Dec. 12, 2017

(87) PCT Pub. No.: WO2016/201408
PCT Pub. Date: Dec. 15, 2016

(65) Prior Publication Data
US 2018/0364163 A1 Dec. 20, 2018

Related U.S. Application Data

(60) Provisional application No. 62/175,050, filed on Jun. 12, 2015, provisional application No. 62/321,542, filed on Apr. 12, 2016.

(51) Int. Cl.
*G01N 21/552* (2014.01)
*A61B 5/00* (2006.01)
(Continued)

(52) U.S. Cl.
CPC ......... *G01N 21/552* (2013.01); *A61B 5/4255* (2013.01); *G01N 21/3581* (2013.01);
(Continued)

(58) Field of Classification Search
CPC ............... G01N 21/552; G01N 21/553; G01N 2021/3595; G01N 21/3581; G01N 2800/102; G01N 2800/067; A61B 5/4255
See application file for complete search history.

(56) References Cited

U.S. PATENT DOCUMENTS 3,393,603 A    7/1968   Harrick
4,602,869 A    7/1986   Harrick
(Continued)

FOREIGN PATENT DOCUMENTS

WO    WO-9517092 A1 * 6/1995 ........... C07K 14/523
WO    2009/121054 A2    10/2009
(Continued)

OTHER PUBLICATIONS

Ahmad, M., et al., "Butyrate and glucose metabolism by colonocytes in experimental colitis in mice" Gut, 2000. 46(4):493-499.
(Continued)

*Primary Examiner* — Michael P LaPage
(74) *Attorney, Agent, or Firm* — Meunier Carlin & Curfman LLC

(57) ABSTRACT

Disclosed are methods, systems, and apparatuses for non-invasive detection of colitis in a subject. The methods involve depositing a bodily fluid sample from the subject on an internal reflection element (IRE). A beam of infrared (IR) radiation can then be directed through the IRE under con-
(Continued)

ditions such that the IR radiation interacts with the bodily fluid sample. An absorption spectrum can then be recorded over a range of preselected frequencies to detect peaks that are affected by colitis. In preferred embodiments, the methods and systems involve Fourier Transform Infrared Spectroscopy (FTIR).

7 Claims, 11 Drawing Sheets

(51) Int. Cl.
  *G01N 21/3581* (2014.01)
  *G01N 21/35* (2014.01)
(52) U.S. Cl.
  CPC ........... *G01N 2021/3595* (2013.01); *G01N 2800/067* (2013.01); *G01N 2800/102* (2013.01)

(56) References Cited

U.S. PATENT DOCUMENTS

| | | | |
|---|---|---|---|
| 6,395,538 B1* | 5/2002 | Naughton | C12M 41/32 435/288.7 |
| 8,614,419 B2 | 12/2013 | Buffington et al. | |
| 2004/0121491 A1* | 6/2004 | Marchand-Brynaert | G01N 21/552 436/527 |
| 2004/0133086 A1 | 7/2004 | Ciurczak et al. | |
| 2010/0130868 A1* | 5/2010 | Hargrove | A61B 5/0075 600/473 |
| 2016/0305877 A1* | 10/2016 | Titus | G01N 21/552 |

FOREIGN PATENT DOCUMENTS

| | | |
|---|---|---|
| WO | 2014/076480 A1 | 5/2014 |
| WO | 2015/085056 A1 | 6/2015 |

OTHER PUBLICATIONS

Argov, S, et al., "inflammatory Bowel Diseases as an Intermediate Stage between Normal and Cancer: A FTIR-Microspectroscopy Approach" Biopolymers. 2004 75(5):384-92.
Ariyawansa, G., et al., "Multi-colored tunneling quantum dot infrared photodetectors operating at room temperature" Infrared Physics & Technology, 2007. 50(2-3):156-161.
Chassaing, B., et al, "Dextran sulfate sodium (DSS)-induced colitis in mice": Current Protocols in Immunology. John Wiley & Sons, Inc, Hoboken, NJ; 2014 (15.25.1-15.25.14).
Chassaing, B., et al., "Fecal Lipocalin 2, a Sensitive and Broadly Dynamic Non-Invasive Biomarker for Intestinal Inflammation" PloS one, 2012. 7(9):e44328.
Clapper, M.L., et al., "Dextran sulfate sodium-induced colitis-associated neoplasia: a promising model for the development of chemopreventive interventions" Acta pharmacologica Sinica, 2007. 28(9):1450-1459.
Friedman, S, et al. "Screening and Surveillance Colonoscopy in Chronic Crohn's Colitis" Gastroenterology. 2001 120(4):820-6.
International Search Report and Written Opinion issued in related International Application No. PCT/US2016/037172 dated Sep. 1, 2016.
Jayaweera, P.V.V., et al., "Displacement currents in semiconductor quantum dots embedded dielectric media: A method for room temperature photon detection" Applied Physics Letters, 2007. 91(6):063114.
Kennedy, R., et al., "Interleukin 10-deficient colitis: new similarities to human inflammatory bowel disease" British journal of surgery, 2000. 87(10):1346-1351.
Kim, J.J., et al., "Investigating Intestinal Inflammation in DSS-induced Model of IBD" Journal of Visualized Experiments : JoVE, 2012(60):3678.
Kornbluth A, et al.: "How effective is current medical therapy for severe ulcerative and Crohn's colitis? An analytic review of selected trials." J Clin Gastroenterol. 1995 20(4):280-4.
Laroui, H., et al., "Dextran Sodium Sulfate (DSS) Induces Colitis in Mice by Forming Nano-Lipocomplexes with Medium-Chain-Length Fatty Acids in the Colon" PloS one, 2012. 7(3):e32084.
Maconi, G., et al., "Glucose intolerance and diabetes mellitus in ulcerative colitis: Pathogenetic and therapeutic implications" World Journal of Gastroenterology : WJG, 2014. 20(13):3507-3515.
Movasaghi, Z., et al. "Fourier Transform Infrared (FTIR) Spectroscopy of Biological Tissues" Applied Spectroscopy Reviews, 2008. 43(2):134-179.
Nykänen, P., "Degradation of thymidine to thymine by rheumatoid arthritis synovial tissue eluate" Scandinavian journal of immunology, 1979. 9(5):477-482.
Perera, A., et al., "High operating temperature split-off band infrared detectors" Applied Physics Letters, 2006. 89(13):131118.
Perera, A.G.U., et al., "Room temperature nano- and microstructure photon detectors" Microelectronics Journal, 2009. 40(3):507-511.
Perše, M. and A. Cerar, "Dextran sodium sulphate colitis mouse model: Traps and tricks" Journal of biomedicine & biotechnology, 2011. 2012:718617-718617.
Petibois, C., et al., "Determination of Glucose in Dried Serum Samples by Fourier-Transform Infrared Spectroscopy" Clinical chemistry, 1999. 45(9):1530-1535.
Schicho, R., et al., "Quantitative Metabolomic Profiling of Serum and Urine in DSS-induced Ulcertive Colitis of Mice by 1H NMR Spectroscopy" Journal of Proteome Research, 2010. 9(12):6265-6273.
Schreyer, A, et al., "Comparison of magnetic resonance imaging colonography with conventional colonoscopy for the assessment of intestinal inflammation in patients with inflammatory bowel disease: a feasible study" Gut. 2005 54(2):250-6.
Teague, R., et al. "Changes in Monosaccharide Content of Mucous Glycoproteins in Ulcerative Colitis" BMJ, 1973. 2(5867):645-646.
Titus, J., et al., "Early detection of cell activation events by means of attenuated total reflection Fourier transform infrared spectroscopy" Applied Physics Letters, 2014. 104(24):243705.
Viennois, E., et al., "Micheliolide, a new sesquiterpene lactone that inhibits intestinal inflammation and colitis-associated cancer" Laboratory Investigation, 2014. 94(9):950-965.
Viennois, E. et al., "Longitudinal study of circulating protein biomarkers in inflammatory bowel disease" Journal of proteomics 2015, 112:166-179.
Vijay-Kumar, M., et al., "Metabolic Syndrome and Altered Gut Microbiota in Mice Lacking Toll-Like Receptor 5" Science, 2010. 328(5975):228-231.
Yu, C. and J. Irudayaraj, "Spectroscopic Characterization of Microorganisms by Fourier Transform Infrared Microspectroscopy" Biopolymers, 2005. 77(6):368-377.
Extended European Search Report, dated Dec. 3, 2018.
Uemera T. et al.: "Non-Invasive Blood Glucose Measurement by Fourier Transform Infrared Spectroscopic Analysis Through the Mucous Membrane of the Lip: Application of a Chalcogenide Optical Fiber System," Frontiers of Medical and Biological Engineer, VLP. Zeist, NL, vol. 9, No. 2, 1999 (1999), pp. 137, 153.
Xiang et al.: Identification of Colitis and Cancer in Colon Biopsies by Fourier Transform Infrared Spectroscopy and Chemometrics, The Scientific World Journal, vol. 2012, pp. 1-4.

\* cited by examiner

ATR-FTIR FOR NON-INVASIVE DETECTION OF COLITIS

CROSS-REFERENCE TO RELATED APPLICATIONS

This application is a national stage application filed under 35 U.S.C. § 371 of PCT/US2016/037172, which claims benefit of U.S. Provisional Application No. 62/175,050, filed Jun. 12, 2015, and application Ser. No. 62/321,542, filed Apr. 12, 2016, which are hereby incorporated herein by reference in their entirety.

STATEMENT REGARDING FEDERALLY SPONSORED RESEARCH OR DEVELOPMENT

This invention was made with Government Support under Grant Nos. DK071594 and DK064711 awarded by the National Institutes of Health. The Government has certain rights in the invention.

BACKGROUND

Inflammatory disorders of the gastrointestinal tract are caused due to environmental or genetic factors. Some of the Inflammatory bowel diseases (IBD) such as ulcerative colitis (Kornbluth A, et al. J Clin Gastroenterol. 1995 20(4):280-4) and Crohn's disease (Friedman, S, et al. Gastroenterology. 2001 120(4):820-6) are debilitating and can lead to life threatening complications such as colorectal cancer (Argov, S, et al. Biopolymers. 2004 75(5):384-92). Assessment of intestinal inflammation in IBD remains a difficult challenge (Schreyer, A, et al. Gut. 2005 54(2):250-6). Currently, the clinical diagnosis of IBD is achieved through colonoscopy, which is used to assess the endoscopic appearance of the colon. However, this technique is not ideal for monitoring disease activity regularly or as an annual checkup and is expensive, invasive requiring sedation with probable complications. Thus, there is a need for new, low risk, simple, inexpensive and objective tools for IBD diagnostics especially for annual checkups.

SUMMARY

Disclosed are methods, systems, and devices for non-invasive detection of inflammatory disease, e.g., colitis, in a subject. The disclosed method can involve depositing a sample from the subject on an internal reflection element (IRE). In some embodiments the sample is allowed to dry. A beam of infrared (IR) radiation can then be directed through the IRE under conditions such that the IR radiation interacts with the bodily fluid sample. In some embodiments, the IR radiation is an evanescent wave with an average penetration depth of about 2 µm. An absorption spectrum can then be recorded over a range of preselected frequencies. This absorption spectrum can then be compared to a control spectrum to identify spectral events associated with colitis.

In some embodiments, the IRE is an attenuated total reflectance (ATR) crystal comprising an optical material with a higher refractive index than the sample comprising the plurality of cells. For example, the IRE can be a germanium, zinc selenide, silicon, diamond, or KRS-5 crystal.

In preferred embodiments, the methods and systems involve Fourier Transform Infrared Spectroscopy (FTIR). Therefore, the disclosed methods and systems can further comprise Fourier transformation of the absorbance spectrum. In some embodiments, the ATR crystal is used with a diffractive monochromator instead of an FTIR.

The range of preselected frequencies for recording absorbance can be between 50 $cm^{-1}$ and 3700 $cm^{-1}$. In some embodiments, peaks at approximately 1033 $cm^{-1}$, 1076 $cm^{-1}$, 1292 $cm^{-1}$, 1704 $cm^{-1}$, or a combination thereof, are an indication of colitis in the subject. Subjects with colitis have higher absorbance at spectral markers 1704 $cm^{-1}$, 1033 $cm^{-1}$ and 1076 $cm^{-1}$. An increase in absorbance is seen in arthritic sera samples at 1704 $cm^{-1}$ and 1033 $cm^{-1}$ (similar to colitic samples), but not at 1076 $cm^{-1}$. Arthritis can be specifically detected by monitoring absorbance at 1292 $cm^{-1}$.

In some embodiments, the sample is bodily fluid sample from a subject suspected of having an inflammatory disease or disorder, e.g., colitis or other inflammatory bowel disorder. The disclosed method can further involve examining the subject by colonoscopy or treating the subject if colitis is indicated.

The details of one or more embodiments of the invention are set forth in the accompanying drawings and the description below. Other features, objects, and advantages of the invention will be apparent from the description and drawings, and from the claims.

Figures 5A, 5B, 5C, 5D:
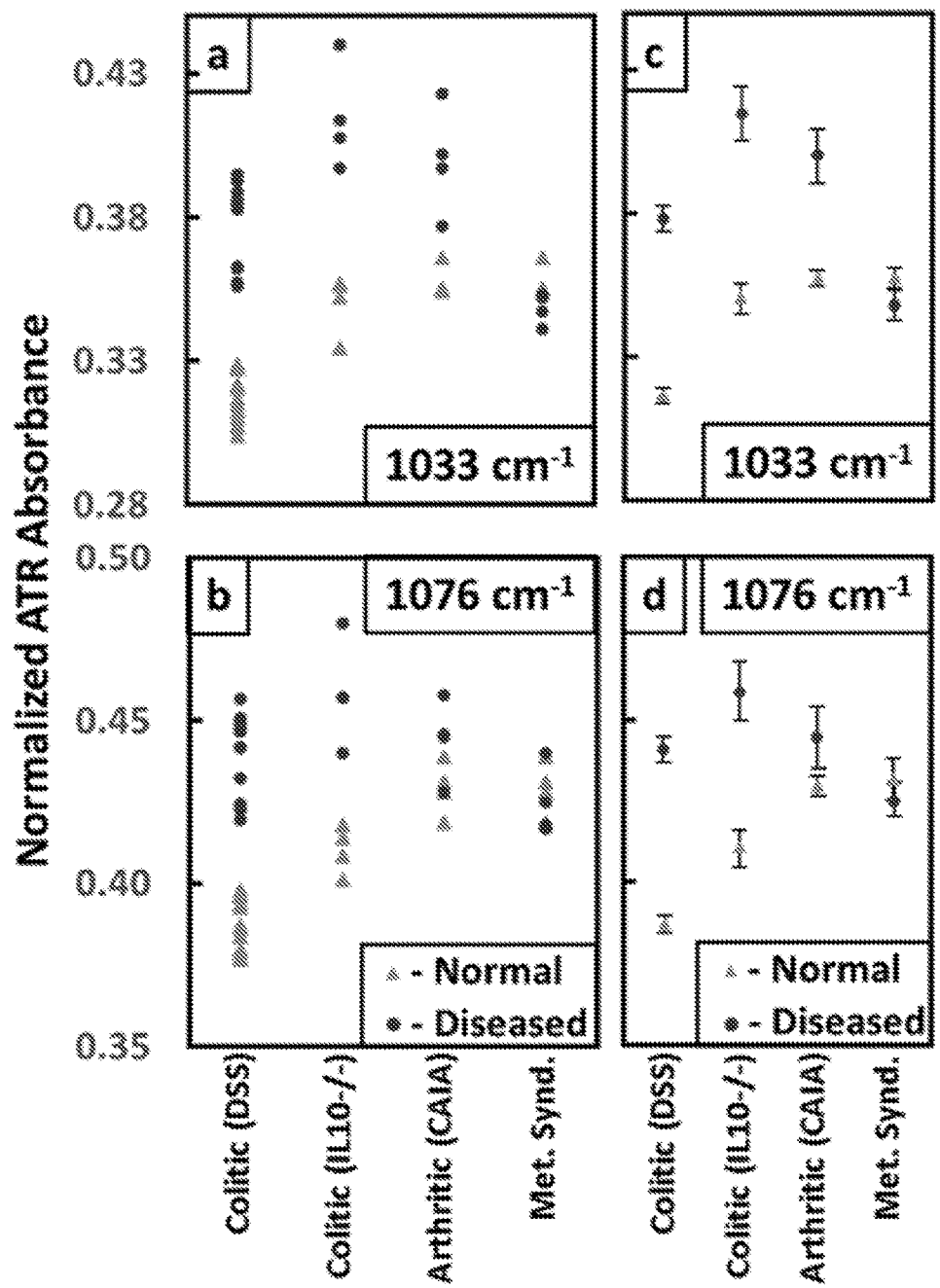

FIGS. 5A and 5B show plots of the absorbances for the glucose peak (FIG. 5A) at ~1033 cm$^{-1}$ and the mannose peak (FIG. 5B) at ~1076 cm$^{-1}$ for Colitic (DSS), Colitic (IL10−/−), Arthritic (CAIA) and Metabolic syndrome samples. FIGS. 5C and 5D show the average values of absorbances for the normal and diseased samples with the error bars. The error bars associated with the normal samples are much smaller than the diseased samples as expected. The metabolic syndrome samples do not show a separation from the normal at either of the two peaks. However especially for colitis samples, there is a clear separation from the normal samples. The absorbance data associated with the peak at ~1033 cm$^{-1}$ for arthritis also show a separation but not at ~1076 cm$^{-1}$. Hence this analysis shows that the absorbance data related to the mannose peak at ~1076 cm$^{-1}$ is unique to colitis.

Figure 6:
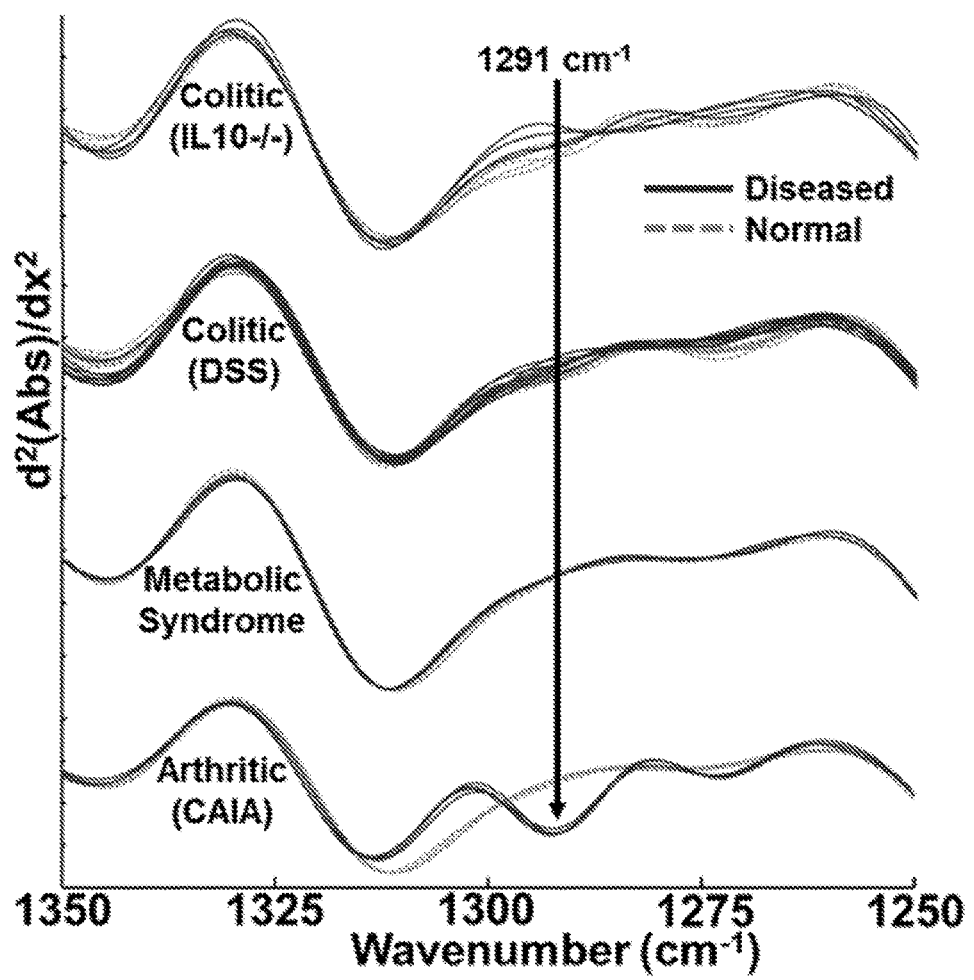

FIG. 6 shows second derivative of the absorbances of colitic (IL10−/− and DSS), metabolic syndrome and arthritic samples clearly indicating the 1292 cm$^{-1}$ peak identified as thymine which is unique to arthritis.

Figure 7:
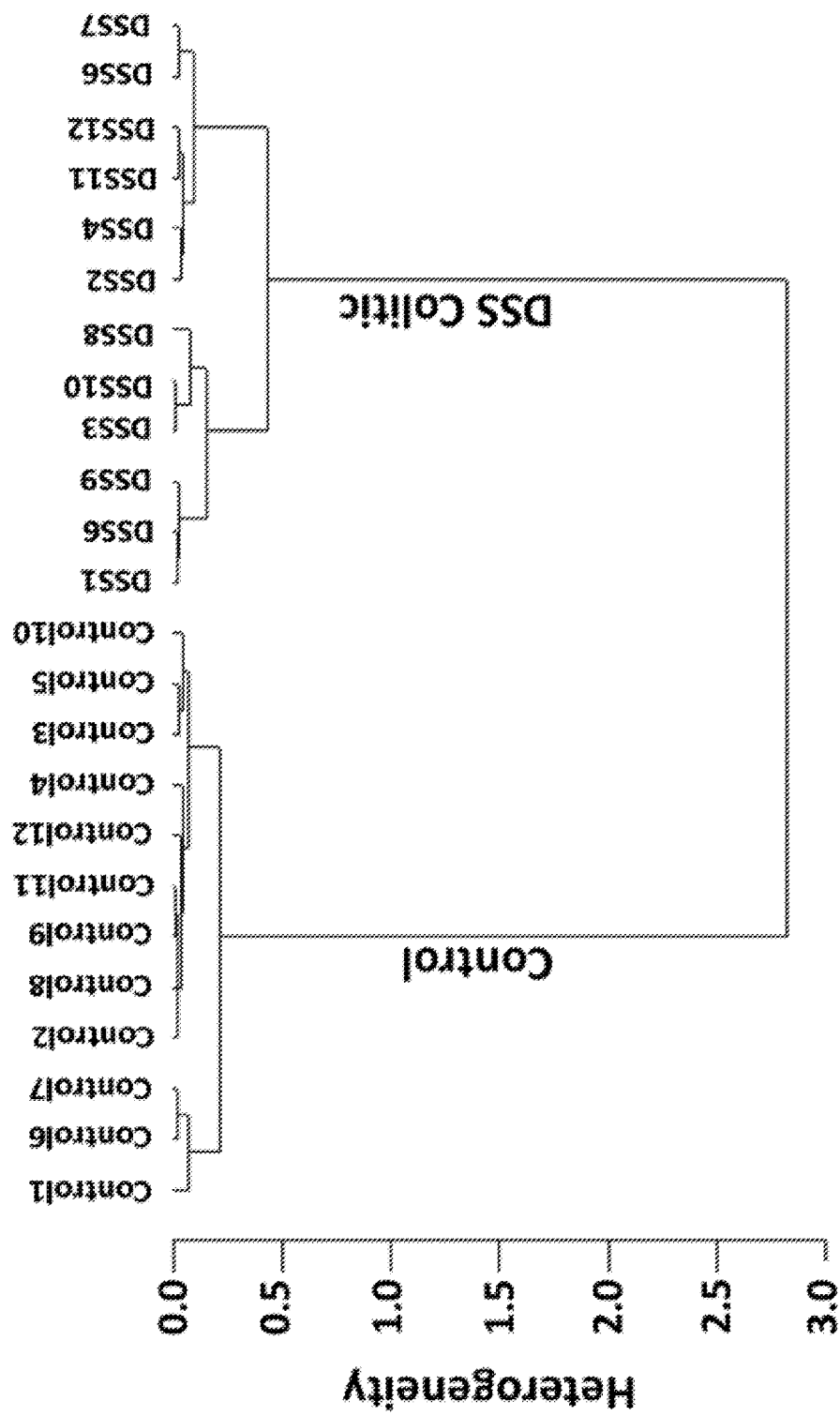

FIG. 7 shows dendrogram plots of the cluster analyses of colitis DSS sample spectra (12 colitic and 12 control) in the range of 1140 to 1000 cm$^{-1}$ to include glucose (1033 cm$^{-1}$) and mannose (1076 cm$^{-1}$) peaks. The spectra are correctly classified into the colitic and control groups based on their conformity to each other. Large heterogeneity is seen between colitis and control samples (2.5) indicating that the two groups are distinctly different. Similar heterogeneity (1.3) is seen in the IL10−/− study.

Figure 8:
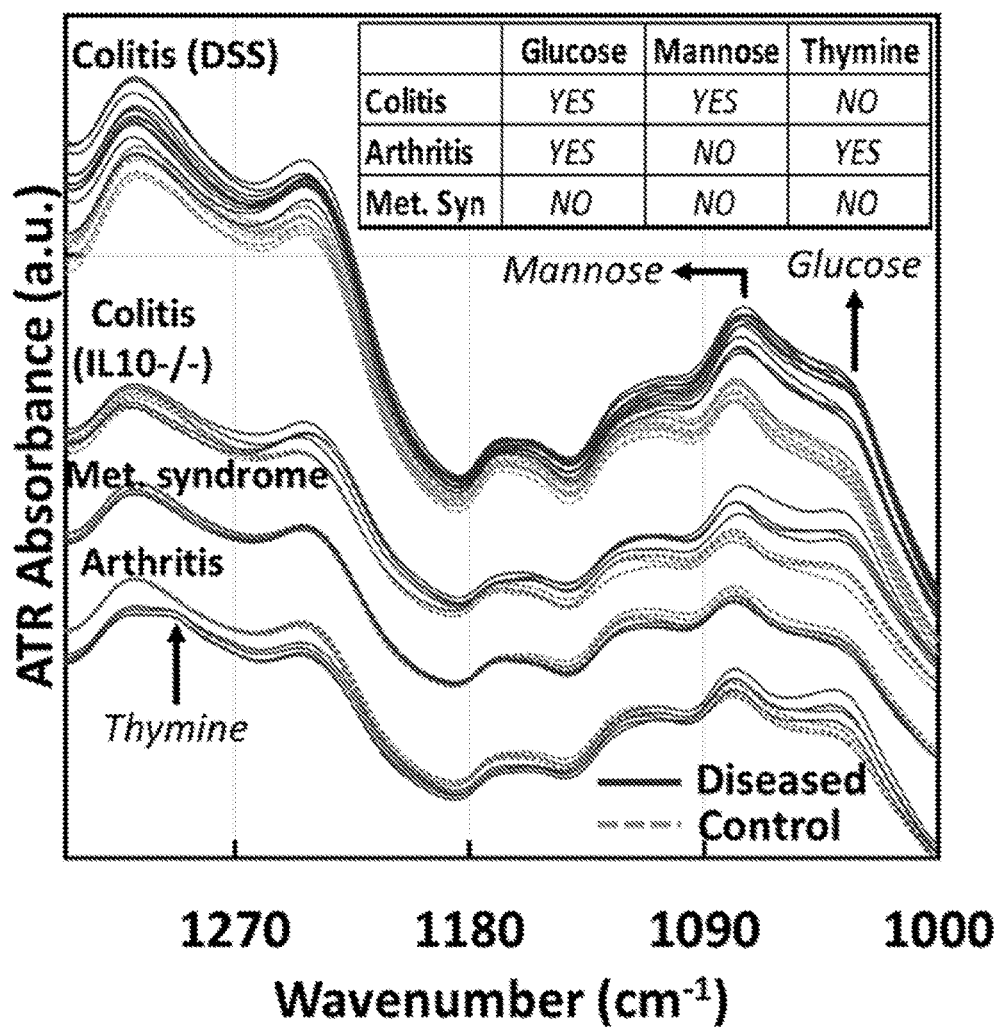

FIG. 8 shows spectra of mice sera before and after developing colitis employing the DSS (n=24) and IL10−/− (n=6) models. Extra-intestinal inflammatory controls namely arthritis and metabolic syndrome were also studied. The signatures (1033 and 1076 cm$^{-1}$) differentiating colitic from non-colitic are identified as glucose and mannose. DSS study had p-values of 4.43 E-8 and 7.59 E-8 at glucose and mannose peaks respectively. Inset (table) shows that the glucose signature is common to colitis and arthritis, but mannose signature is unique to colitis. Arthritis has a unique signature at 1292 cm$^{-1}$ which is identified as thymine (see FIG. 4). All spectra are normalized to the Amide I peak (1642 cm$^{-1}$).

Figure 9:
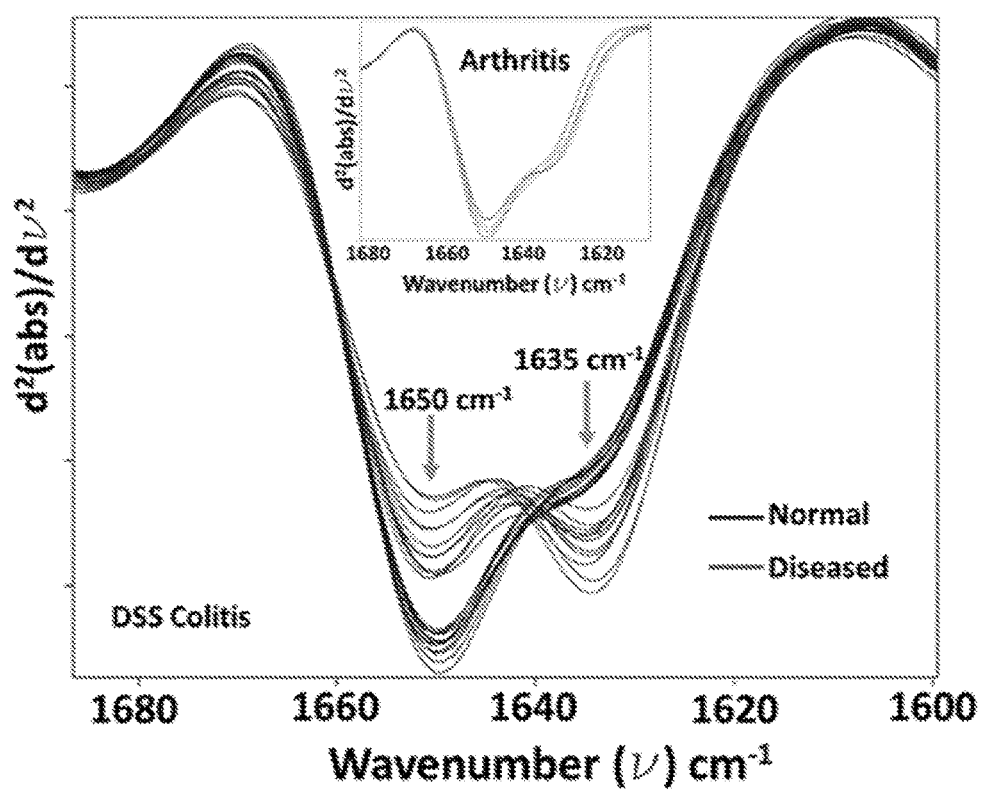

FIG. 9 shows second derivative of the absorbance at the amide I region indicates a significant difference between normal and colitic samples while considering the alpha helix to beta sheet ratios. As seen in the inset, there is no such difference for arthritic model which serves as an extra-inflammatory control for colitis. Thus, the alpha helix:beta sheet (1650:1635 cm$^{-1}$) ratio serves as a screening signature for colitis.

Figure 10:
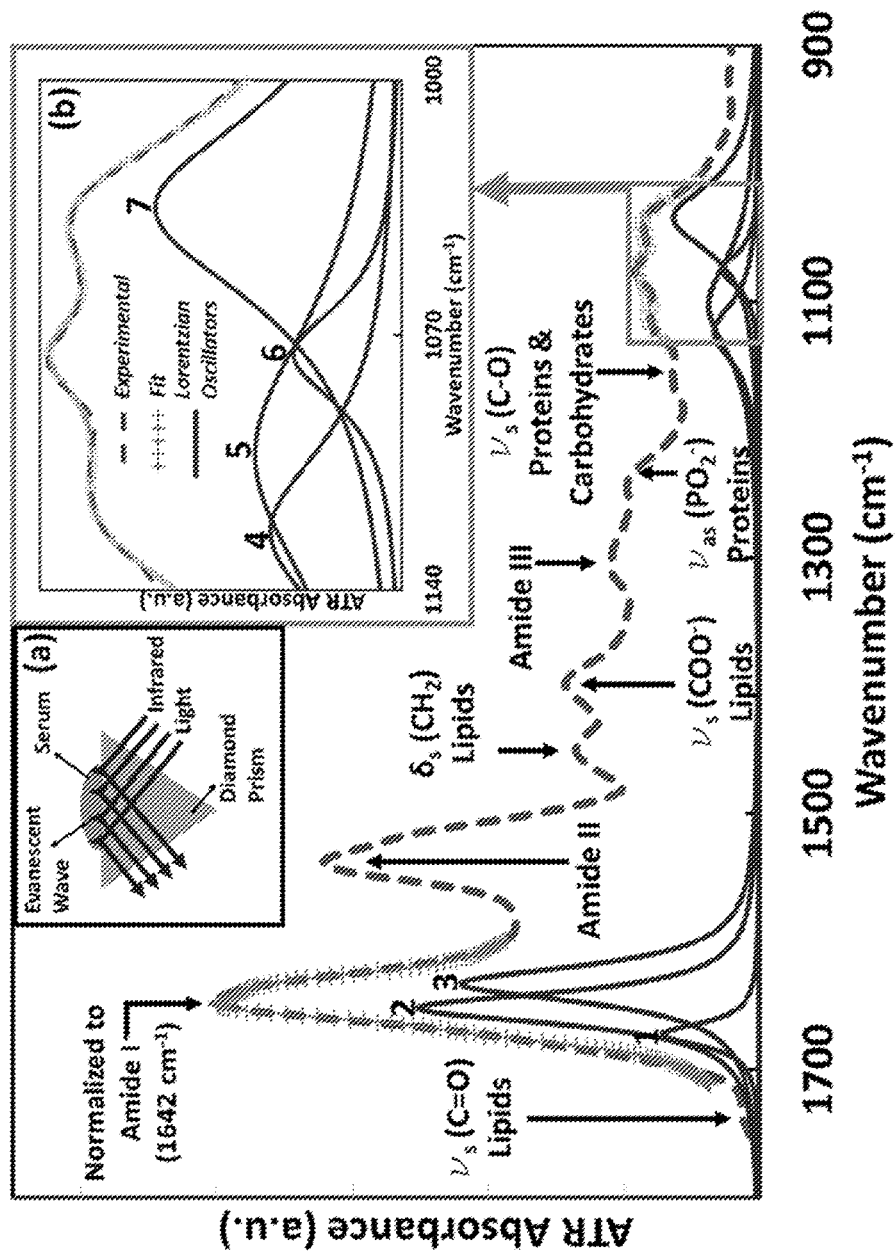

FIG. 10 shows the spectrum of normal mouse serum with the major peaks assigned. Inset (a) shows the schematic working of ATR technique. Spectra can be normalized to Amide I peak at 1642 cm$^{-1}$. The Lorentzian oscillators for amide I and polysaccharides (inset b) and the fittings for the experimental absorbance curve are also shown. The oscillators used are 1: phenyl ring stretch, 2: α-helix, 3: β-sheet, 4 & 5: carbohydrates, 6: mannose, 7: glucose.

DETAILED DESCRIPTION

The disclosed methods involve the use of an infrared spectrum measuring apparatus. In some embodiments, the apparatus comprises: an internal reflecting element (IRE) comprising a reflection face located on the IRE at a region of intended contact between the IRE and a sample; an infrared radiation source for supplying an evanescent wave of infrared radiation and directing the same from the outside of the IRE to the inside thereof so as to cause the infrared radiation to be incident on the reflection face; and a detector for detecting the once-reflected infrared radiation. Representative, but non-limiting examples of instruments that can provide the infrared radiation source include Fourier Transform Infrared Spectroscopy (FTIR) spectrometers.

The term "internal reflection element" or IRE refers to a crystal, prism, or other structure that will admit incoming radiation and reflect the radiation at least once from a surface on the interior of the element, preferably following interaction of the radiation with a sample in contact with the reflecting surface. Following such a reflectance, the radiation can be re-reflected or emitted from the element. Preferably the IRE comprises a germanium crystal, a zinc selenide crystal, or other material with higher index of refraction than the refractive index of the sample being read that are capable of transmitting IR or visible light.

The term "multi-pass ATR" refers to an attenuated total reflectance technique in which radiation that is incident on an internal reflectance element having two or more reflection faces within the IRE experiences two or more interactions with a reflection face before exiting the IRE. At these interfaces, the light is totally reflected back into the IRE material. Such interactions are typically referred to as "bounces" or "passes". Application of multi-pass ATR generates a multi-pass ATR spectrum. Typically, the IRE is in contact with a sample, the incident radiation is IR radiation and the exiting radiation subsequently interacts with a detector.

The term "single-pass ATR" refers to an attenuated total reflectance technique in which radiation incident on an internal reflectance element (IRE) having one or more reflection faces within the IRE experiences only one interaction with a reflection face before exiting the IRE. At this interface, the light is totally reflected back into the IRE material. Application of single-pass ATR generates a single-pass ATR spectrum.

The term "reflecting surface" refers to a surface capable of reflecting incident radiation. On the IR surface where the sample is deposited, the incident light is at an angle greater than the critical angle and hence experiences total internal reflection. There is no transmission of light at this interface, but rather an evanescent wave that escapes out of the surface of the IRE but is coupled back into the IRE material. Indeed, the technique of attenuated total internal reflection (ATR) is based on the principle that an evanescent wave interacts with a sample that is within one fifth of one wavelength of the dielectric boundary.

Attenuated total reflection (ATR) spectroscopy is predicated on the concept that, when light traveling within a medium impinges upon an interface between that medium and a medium of lower refractive index, it either passes into the second medium or is totally internally reflected, depending on whether the quantity $[n_1/n_2 \sin \theta_i]$ is less than or greater than one. In this relationship, $n_1$ and $n_2$ are the refractive indices of the first and second media, respectively, and $\theta_i$ is the angle of incidence. If $n_1/n_2 \sin \theta_1$ is greater than one, total internal reflection occurs. Although the internal reflection is referred to as total, the light, during the reflection process, penetrates a short distance into the second medium. The depth of penetration depends in a predictable fashion on the refractive indices of the two media and the angle of incidence, and is typically on the order of tenths of the wavelength of the light. If the incident light includes a wavelength absorbed by a constituent of the second medium, light of such wavelength will be partially absorbed or attenuated during reflection due to the penetration of the light into the second medium. This effect is referred to as attenuated total reflection. Due to the very shallow penetration of the light into the second medium, ATR is a useful technique for measuring absorbance by strongly absorbing materials. ATR has also been particularly useful for measuring absorbance of material deposited on a surface. Attenuated total reflection spectroscopy is widely used to collect an absorption spectrum from samples that are too opaque for direct absorption measurements.

In practice, one surface of an internal reflecting element (IRE) is placed in contact with a test sample. An incident beam of radiation is directed through the IRE so that it is totally internally reflected at the boundary between the IRE and the test sample. Some of the energy of the incident radiation is absorbed by the test sample through evanescent coupling. The amount of absorption is representative of the molecular structure and/or the molecular species found in the test sample. The reflected radiation, therefore, includes information from which an absorption spectrum for the test sample can be acquired. IREs utilizing total internal reflection or attenuated total reflection principles are commonly found in optical systems designed to analyze samples by assessing the optical constants of the sample and by establishing the physical and chemical composition thereof. Examples of IREs disposed in various optical systems are shown, for example, in U.S. Pat. Nos. 4,602,869 and 3,393,603. In some embodiments, the IRE is a germanium crystal or a zinc selenide crystal. The angle of incidence is defined as the angle between the ray direction and the normal to the surface. A 45-degree angle of incidence is often convenient for a multi-pass FTIR-ATR element. However, the angle of incidence and the composition of an element can be varied to optimize the parameters for a given experiment.

In ATR-FTIR spectroscopy, light is totally internally reflected inside a prism of high refractive index (FIG. 8, inset a). Photons come out of the crystal penetrating the sample, and then are coupled back into the system. This evanescent wave can interact with the material on the surface of the crystal (diamond in this case). The intensities of the frequencies of light measured after passing through the prism are highly sensitive to the materials present on the surface of the crystal. The penetration depth of the photons, a function of the wavelength of light and the refractive indices of the ATR crystal and sample, is about two microns at 1000 $cm^{-1}$ wavenumber. The Bruker vertex 70 spectrometer can cover the range from 15800 to 10 $cm^{-1}$ with a spectral resolution between 0.25 to 256 $cm^{-1}$ and specific number of scan averages can be selected as needed depending on the signal/noise ratio. The serum sample can be deposited on the crystal surface and allowed to air dry (approximately seven minutes) before obtaining the ATR absorbance spectrum (FIG. 8). The specific features of the spectra can be simulated by using Lorentzian oscillators corresponding to the expected individual components. The amide I peak can be fitted with oscillators 1, 2 and 3. Spectra can be normalized to the Amide I peak (1642 $cm^{-1}$) which is the commonly used standard in spectroscopy studies involving biological samples. The amide I and the polysaccharides regions can be simulated by using Lorentzian oscillators corresponding to the expected individual components (1,2,3 and 4,5,6,7) with the RMS error as low as 0.004. This can allow one to match the colitic (polysaccharides) spectra with the known concentrations.

Mathematical and statistical operations that are performed in the course of practicing the present methods can be performed using any suitable computational equipment and software. For example, a commercially available personal computer can be used as a platform for software that can facilitate the acquisition of data, the calculation of difference spectra and perform spectral and other analysis. Computers networked with an FTIR instrument can be employed to acquire data on one machine and process it on another. Suitable data acquisition and management software packages can be designed and written de novo or can be purchased. Suitable commercially available software packages can include SCANTRAQ BASIC™ software package available from FTG Software Associates of Princeton, N.J., and GRAMS/32™ Version 5.2 software package, available from ThermoGalactic of Salem, N.H.

In some embodiments, the process of acquiring a spectrum of a sample is automated.

Suitable commercially available software packages for automated spectrum acquisition include the WINFIRST™ package available from Thermo Mattson of Madison, Wis., and the AUTOPRO™ software package available from Pike Technologies, Inc. of Madison, Wis. These software packages can be employed to automate spectrum acquisition and can be useful for analyzing large numbers of samples. In some embodiments, the process is fully automated and can comprise an autosampler to inject and remove samples and a spectrum acquisition software package to run an FTIR microscope or FTIR bench accessory. Additionally, the identified software packages can be modified, or software can be written or purchased, to perform the various mathematical and statistical operations that can be performed when acquiring data by employing the present inventive methods. For example, software can be provided and employed to analyze an acquired spectrum, whereby the water component is automatically subtracted from the spectrum and the quality and quantity of secondary structure is subsequently identified using algorithms referred to, incorporated and disclosed herein. In this embodiment, a researcher can simply prepare the autosampler, configure the software and begin the process.

Inflammatory abnormalities are a large group of disorders that underlie a vast variety of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease.

Rheumatoid arthritis (RA) is a chronic, systemic inflammatory disorder that primarily affects joints. It may result in deformed and painful joints, which can lead to loss of function. The disease may also have signs and symptoms in organs other than joints.

Inflammatory bowel disease (IBD) is a group of inflammatory conditions of the colon and small intestine. Crohn's disease and ulcerative colitis are the principal types of inflammatory bowel disease. It is important to note that not only does Crohn's disease affect the small intestine and large intestine, it can also affect the mouth, oesophagus, stomach and the anus whereas ulcerative colitis primarily affects the colon and the rectum.

In spite of Crohn's and UC being very different diseases, both may present with any of the following symptoms: abdominal pain, vomiting, diarrhea, rectal bleeding, severe internal cramps/muscle spasms in the region of the pelvis and weight loss. Anemia is the most prevalent extraintestinal complication of inflammatory bowel disease. Associated complaints or diseases include arthritis, pyoderma gangrenosum, primary sclerosing cholangitis, and non-thyroidal illness syndrome (NTIS). Associations with deep vein thrombosis (DVT) and Bronchiolitis obliterans organizing pneumonia (BOOP) have also been reported.

Once the disclosed method indicates the presence of an IBD, diagnosis can be confirmed by biopsy on colonoscopy.

Medical treatment of IBD is individualized to each patient. The choice of which drugs to use and by which route to administer them (oral, rectal, injection, infusion) depends on factors including the type, distribution, and severity of the patient's disease, as well as other historical and biochemical prognostic factors, and patient preferences. For example, mesalazine is more useful in ulcerative colitis than in Crohn's disease. Generally, depending on the level of severity, IBD may require immunosuppression to control the symptom, such as prednisone, TNF inhibition, azathioprine (Imuran), methotrexate, or 6-mercaptopurine.

Often, anti-inflammatory steroids are used to control disease flares and were once acceptable as a maintenance drug. In use for several years in Crohn's disease patients and recently in patients with ulcerative colitis, biologicals have been used such as TNF inhibitors. Severe cases may require surgery, such as bowel resection, strictureplasty or a temporary or permanent colostomy or ileostomy. Ulcerative colitis can in most cases be cured by proctocolectomy, however this may not eliminate extra-intestinal symptoms. A small percentage of patients with ileo-anal pouches do have to manage occasional or even chronic pouchitis. In Crohn's disease, surgery involves removing the worst inflamed segments of the intestine and connecting the healthy regions, but unfortunately, it does not cure Crohn's or eliminate the disease, as at some point after the first surgery, Crohn's disease recurs in the healthy parts of the intestine, usually at the resection site. (For example, if a patient with Crohn's disease has an ileocecal anastomosis, in which the caecum and terminal ileum are removed and the ileum is joined to the ascending colon, their Crohn's will nearly always flare-up near the anastomosis or in the rest of the ascending colon).

A relatively new treatment option is fecal bacteriotherapy (FBT), which has been used to successfully treat IBD in several small studies.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "sample from a subject" refers to a tissue (e.g., tissue biopsy), organ, cell (including a cell maintained in culture), cell lysate (or lysate fraction), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Minimally Invasive Screening for Colitis Using Attenuated Total Internal Reflectance Fourier Transform Infrared Sectroscopy Materials and Methods Mice Three week-old female C57BL/6 wild type (WT) and interleukin 10 knockout (IL10−/−) mice were obtained from Jackson Laboratories (Bar Harbor, Me.). Toll-like receptor knockout (TLR5−/−) mice were grown in our facility. Mice were group housed under a controlled temperature (25° C.) and photoperiod (12:12-h light-dark cycle) and fed ad libitum. All studies were performed in accordance with the Institutional Animal Care and Use Committee at Georgia State University (Atlanta, Ga.), permit number: A14010.

Development of Colitis in IL10−/−

IL10−/− mice develop colitis on a time dependent manner In order to assess the intestinal inflammation in those mice at different times of colitis development, feces were collected at week 4 and week 14 to measure Lcn-2. Blood was collected at week 4 and 14 to obtain sera by centrifugation using serum separator tubes (BD Biosciences, Franklin Lakes, N.J.)

Dextran Sodium Sulphate (DSS) Induced Colitis

C57BL/6 WT mice were administered DSS (MP Biomedicals, Solon, Ohio) at 3% in drinking water ad libitum for 7 days. Feces and blood were collected at day 0 (before DSS treatment) and day 7. Hemolysis-free serum was collected by centrifugation using serum separator tubes. Mice were sacrificed by $CO_2$ euthanasia.

Collagen Antibody-Induced Arthritis Model

BALB/C WT mice received collagen antibodies injections (200 μL) on day 0 by an intravenous injection (tail vein). On day 6, mice received a lipopolysaccharide (LPS) boost injection (200 μL) by intraperitoneal injection. Blood samples were collected from each mouse on pretreatment (day −2) and on day 12 from the jugular vein. Hemolysis-free serum was collected by centrifugation using serum separator tubes.

TLR5−/− Model of Metabolic Syndrome

TLR5−/− spontaneously develop metabolic syndrome as previously described (Vijay-Kumar, M., et al., Science, 2010. 328(5975):228-231). Age-matched WT and TLR5−/− mice were fasted for 5-h and baseline blood glucose levels measured with a blood glucose meter (Roche) using blood collected from the tail vein.

H&E Staining of Colonic Tissue

Mouse colons were fixed in 10% buffered formalin for 24 hours at room temperature and then embedded in paraffin. Tissues were sectioned at 5-μm thickness and stained with hematoxylin & eosin (H&E) using standard protocols. Images were acquired using a Zeiss Axioskop 2 plus microscope (Carl Zeiss MicroImaging) equipped with an Axio-Cam MRc5 CCD camera (Carl Zeiss).

Quantification of Fecal and Serum Lcn-2 by ELISA

Fecal samples were reconstituted in PBS containing 0.1% Tween 20 (100 mg/me. After centrifugation, clear supernatants were collected. Serum samples were diluted in kit-recommended reagent diluent (1.0% BSA in PBS). Lipocalin-2 (Lcn-2) levels were estimated in the supernatants and/or serum using Duoset murine Lcn-2 ELISA kits (R & D Systems, Minneapolis, Minn.).

Colonic Myeloperoxidase (MPO) Assay

Neutrophil influx in colon was analyzed as marker of inflammation by assaying the enzymatic activity of MPO, a neutrophils marker. Briefly, tissue (50 mg/mL) was thoroughly washed in PBS and homogenized in 0.5% hexadecyltrimethylammonium bromide (Sigma, St. Louis, Mo.) in 50 mM PBS, (pH 6.0), freeze-thawed 3 times, sonicated and centrifuged. MPO was assayed in the clear supernatant by adding 1 mg/mL of dianisidine dihydrochloride (Sigma) and 0.0005% $H_2O_2$ and the change in optical density measured at 450 nm. Human neutrophil MPO (Sigma) was used as standard. One unit of MPO activity was defined as the amount that degraded 1 mmol peroxidase per minute.

Fourier Transform Infrared (FTIR) Spectroscopy

A Bruker Vertex 70 FTIR spectrometer was used to obtain all the spectroscopic results. The samples were scanned covering the wavelength range of 4000 to 400 $cm^{-1}$ and the 1800 to 1000 $cm^{-1}$ section was used for this study. A medium Blackman-Harris appodization was employed with a resolution of 8 $cm^{-1}$. The samples were scanned 50 times and averaged. Each co-added sample scan was repeated 5 times and averaged. A room temperature Deuterated Lanthanum Alanine doped TriGlycine Sulphate (DLaTGS) pyroelectric detector was employed. The infrared light beam intensity was controlled by passing it through a 3 mm aperture. This is done to optimize the detector response and prevent saturation. A Parker-Balston dry air purging system was used to reduce the moisture and carbon dioxide levels of the ambient air in the spectrometer.

Attenuated Total Reflectance (ATR) Configuration

MVP-Pro ATR accessory from Harrick-Scientific was used for all spectroscopic measurements in this study. A diamond crystal (1 mm×1.5 mm) was the internal reflection element configured to have a single reflection of the infrared radiation. A sample of one microliter is deposited on the crystal surface and allowed to air dry (~5 minutes). An evanescent wave with an approximate penetration depth of 2 microns (dependent on the refractive indices of the ATR crystal and sample and the wavelength of light) interacts with the sample. The output spectra is an ATR absorbance spectra which is subsequently analysed.

Post Processing Techniques

The 5 reads of the 50 co-added scans for each sample (total of 250 scans) are averaged. The spectra were sectioned to the 1800 to 1000 $cm^{-1}$ range. Using OPUS 7.2 software, all the spectra were internally normalized (Yu, C. and J. Irudayaraj, Biopolymers, 2005. 77(6):368-377) by scaling the entire sectioned range so that the absorbance value at the 1642 $cm^{-1}$ peak (Amide I) was 2.0. Spectral deconvolution was also done to better resolve the peaks by obtaining the second derivative followed by a 9 point smoothing using Microsoft Excel software.

Data Analysis Techniques

Cluster and heterogeneity analyses were carried out in the spectral range of 1140 to 1000 $cm^{-1}$ using the Bruker Optics OPUS 7.2 software. The algorithm calculates the Euclidean distance between each spectrum and groups them into clusters based on the conformity of the spectra with each other. The resulting data is plotted as a heterogeneity dendrogram chart where the heterogeneity index on the y-axis indicates the degree of heterogeneity between the identified clusters. Student's t-tests were carried out for the DSS study and not for the IL10−/−, CAIA and Metabolic syndrome studies due to the smaller sample sizes, although the uncertainty levels of the averages are shown.

Results

DSS-induced colitis (Laroui, H., et al., PloS one, 2012. 7(3):e32084; Chassaing, B., et al., Current Protocols in Immunology:15.25.1-15.25.14) is a commonly used chemically-induced mouse model of acute colitis which has similarities to ulcerative colitis in human DSS first disrupts the intestinal barrier functions followed by an increase of inflammation which closely resembles histological and clinical characteristics of IBDs such as ulcerative colitis (Clapper, M. L., et al., Acta pharmacologica Sinica, 2007. 28(9):1450-1459; Peše, M. and A. Cerar, Journal of biomedicine & biotechnology, 2011. 2012:718617-718617). The second model studied, IL10−/− mouse model (Kennedy, R., et al., British journal of surgery, 2000. 87(10):1346-1351) closely resembles the physiological, histological and biochemical features of human chronic colitis and develops colitis mediated by T helper cell 1 (Th1) cells. Mice with targeted deletion of the IL10 gene spontaneously develop chronic enterocolitis with massive infiltration of lymphocytes, activated macrophages, and neutrophils in a Th1 cell-mediated mechanism (Kim, J. J., et al., Journal of Visualized Experiments: JoVE, 2012(60):3678). The predictability of the timing of colitis in IL10−/− mice allows longitudinal assessment of blood samples during colitis progression from 4 weeks (no symptoms shown) up to 14 weeks, the age at which the mice display signs of severe colitis.

Figures 1A, 1B:
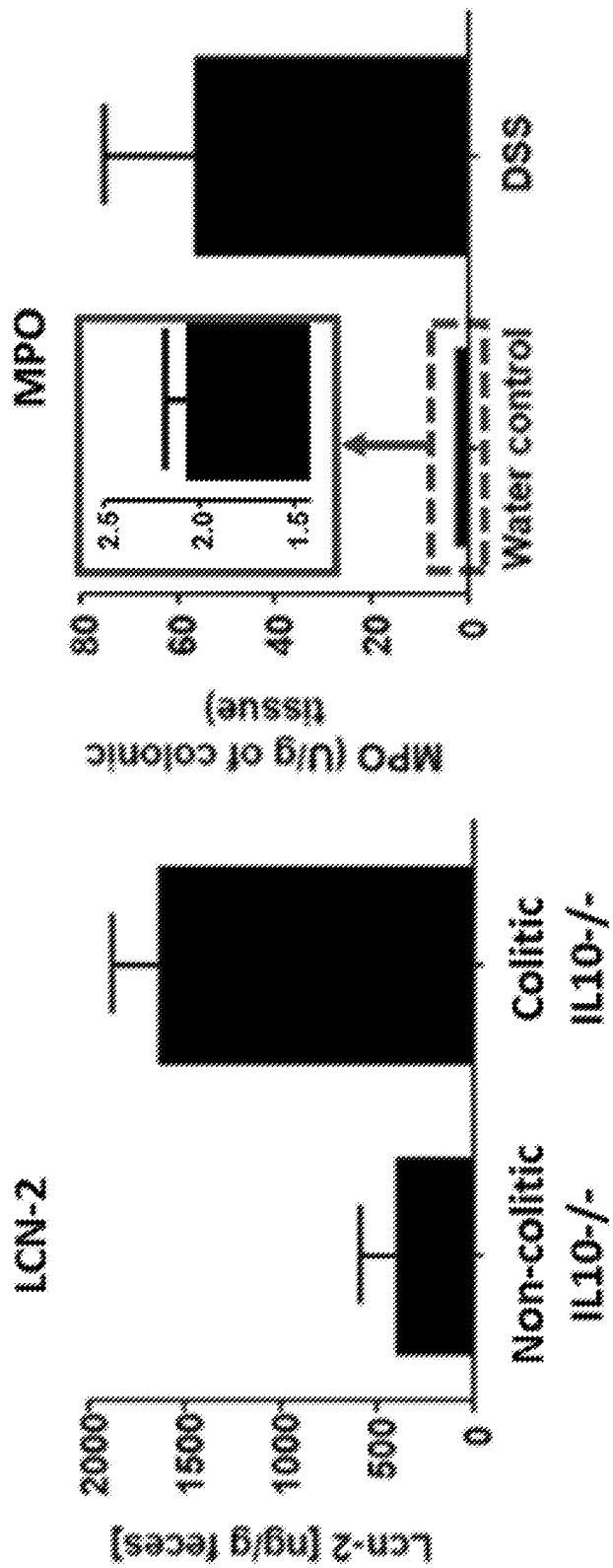
FIG. 1A shows Lcn-2 quantified in the feces of mice showing a clear increase of Lcn-2 in colitic IL10−/− vs. non-colitic IL10−/− mice.
FIG. 1B shows colonic myeloperoxidase (MPO) activity quantified in the distal colon of DSS induced-colitis compared to water control mice agreeing well with the spectroscopy data.
Figure 1C:
FIG. 1C shows respective H&E-stained colons of WT water control, DSS-induced colitis and colitic IL10−/− mice indicate sites of lymphocytes infiltrations (arrow heads) and erosion of the crypt figures (arrows). Scale bar: 100 µm.

To confirm the effectiveness of these two models as tools for investigating spectral markers for colitis, the development of colitis was assessed in these mice using other established techniques. Histological features were assessed by H&E staining, and the degree of inflammation was measured in DSS and IL10−/− model by respectively assessing MPO activity, a marker of inflammation in the colon (Viennois, E., et al., Laboratory Investigation, 2014. 94(9):950-965), and measuring fecal Lipocalin 2 (Lcn-2) levels, previously described (Chassaing, B., et al., PloS one, 2012. 7(9):e44328) as being a robust fecal marker that correlates with the severity of inflammation. MPO is produced by neutrophils, a class of leukocytes that highly infiltrate into the mucosa in a situation of intestinal inflammation. Increases of Lcn-2 levels and MPO activity in the feces of IL10−/− mice (FIG. 1A) and in DSS-induced colitis colon samples (FIG. 1B) respectively, were observed. The increase of lymphocyte infiltration (FIG. 1C, arrow head) and the erosion (FIG. 1c, arrow) of intestinal glands (crypt), observed on the H&E stained picture of the colon confirmed that, in contrast to the control groups (non-colitic), the DSS-treated and the IL10−/− mice develop colitis.

Figure 2:
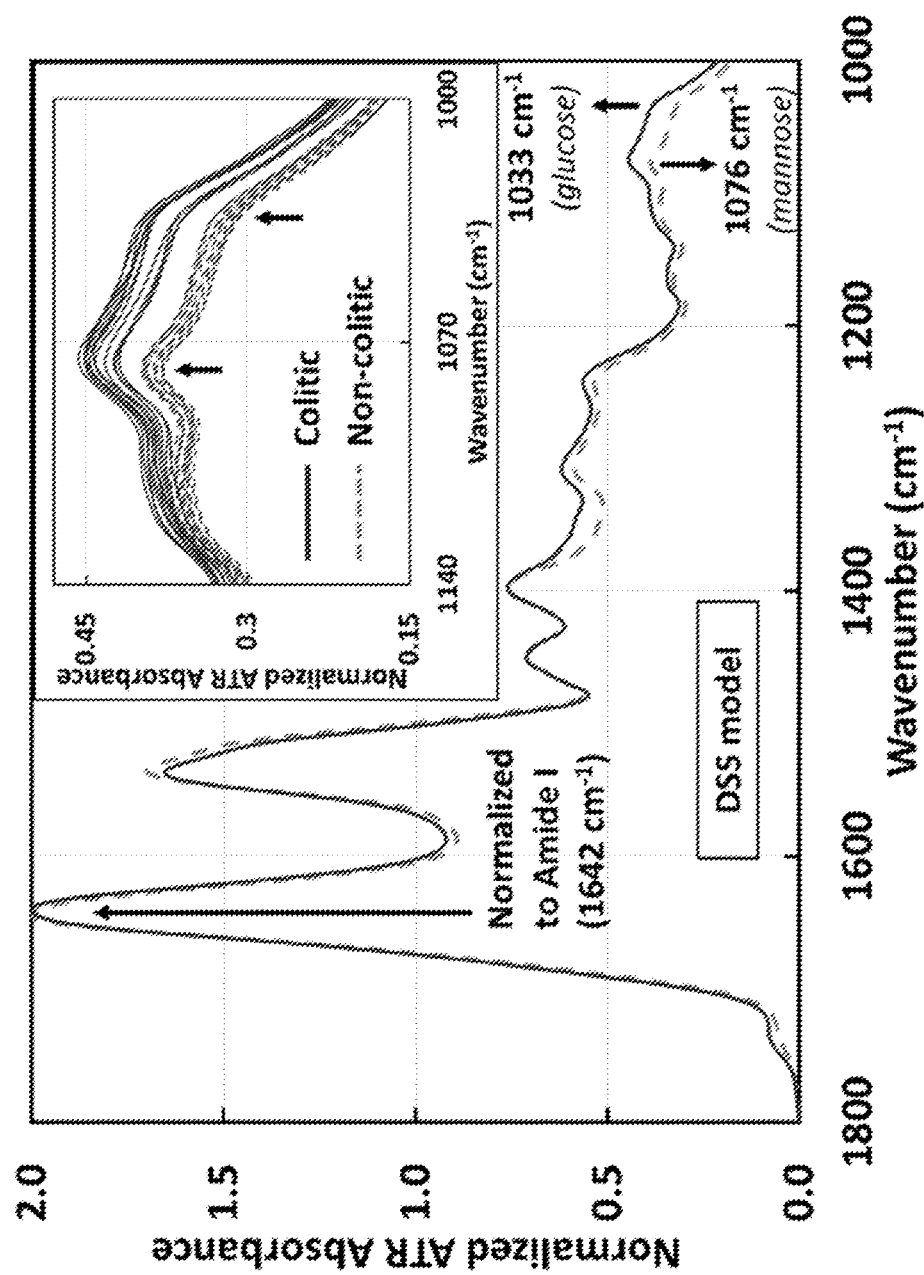
FIG. 2 shows averaged ATR-FTIR spectra of sera drawn from mice before (n=12) and after (n=12) developing colitis induced by 3% DSS. The differentiating markers 1033 and 1076 $cm^{-1}$ are identified as glucose and mannose with p-values of 4.43 E-8 and 7.59 E-8 respectively. The inset shows the individual serum samples from 1140-1000 $cm^{-1}$ for clarity. Individual colitic and non-colitic spectra show a clear separation between the groups. With further data points it should be possible to find an absorbance range for the two groups. All spectra are normalized to the Amide I peak (1642 $cm^{-1}$). The averages for the glucose peak are 0.3175±0.0024 (non-colitic) and 0.3788±0.0041 (colitic) and the averages for the mannose peak are 0.3847±0.0022 (non-colitic) and 0.438±0.0035 (colitic).
Figure 3:
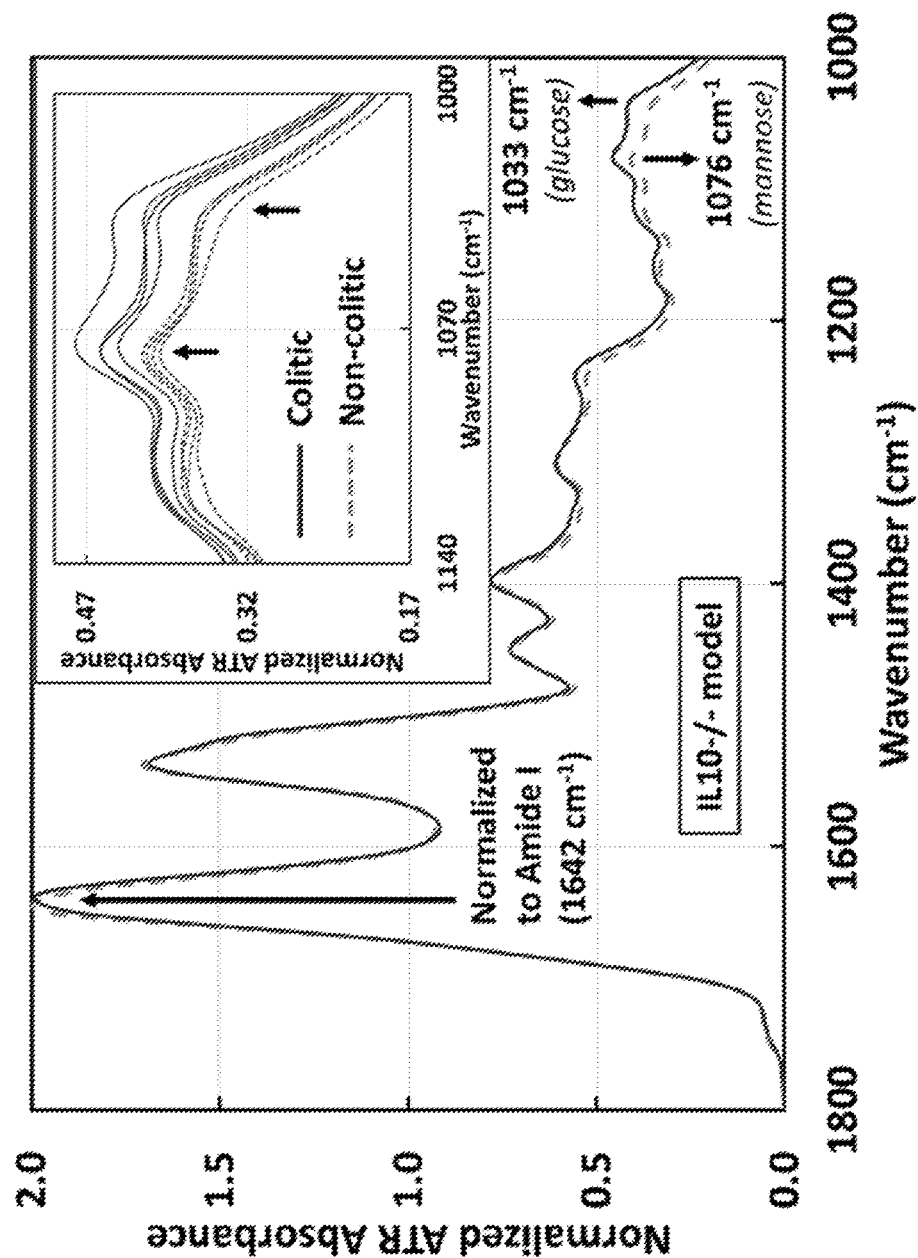
FIG. 3 shows averaged ATR-FTIR spectra of sera drawn from IL10−/− mice before (n=4) and after (n=4) spontaneously developing colitis. The same markers 1033 and 1076 $cm^{-1}$ identified in the DSS model are effective in differentiating colitic from non-colitic spectra of the IL10−/− model. The inset shows the individual serum samples from 1140-1000 $cm^{-1}$ for clarity, again showing a clear separation between the two groups. All spectra are normalized to the Amide I peak (1642 $cm^{-1}$). The averages for the glucose peak are 0.3491±0.0057 (non-colitic) and 0.412±0.009 (colitic) and the averages for the mannose peak are 0.4071±0.0034 (non-colitic) and 0.4553±0.0081 (colitic).

Spectroscopic measurements were performed on sera from DSS-induced colitis mice compared to the same mice before intake of DSS (control mice) and on colitic IL10−/− mice compared to the same mice before the development of colitis. Serum was chosen due to its stability and absence of any additives such as anticoagulants. Serum samples were deposited on the ATR crystal and allowed to dry. By allowing the water in the sera to evaporate, the signal to noise ratio of the spectral signal of other sera components are greatly enhanced, which are otherwise occluded by the broad water absorption. Similar significant differences in absorbance were observed in both DSS (FIG. 2) and IL10−/− (FIG. 3) mouse models between the control groups (non-colitic) and the colitic groups at ~1033 $cm^{-1}$ and ~1076 $cm^{-1}$. Both absorbance peaks have been attributed to the symmetric stretching modes of C—O indicating the presence of saccharides (Movasaghi, Z., et al. Applied Spectroscopy Reviews, 2008. 43(2):134-179), with the vibrational modes at ~1033 $cm^{-1}$ and ~1076 $cm^{-1}$ due to glucose and mannose respectively (Petibois, C., et al., Clinical chemistry, 1999. 45(9):1530-1535).

It has been reported that in colitis serum samples, there is a reduction in butyrate oxidation with a compensatory increase in the oxidation levels of glucose (Ahmad, M., et al., Gut, 2000. 46(4):493-499). Hence, the increase in the absorbance at ~1033 $cm^{-1}$ in colitic serum samples could be an indication of colitis.

Studies in humans have shown the co-occurrence of ulcerative colitis with that of diabetes and glucose intolerance (Maconi, G., et al., World Journal of Gastroenterology: WJG, 2014. 20(13):3507-3515). In order to exclude the possibility that the mannose and glucose peaks obtained for the IL10−/− and DSS-induced models of colitis originate from the co-occurrence of other glucose intolerance conditions, similar assays were performed using a mouse model developing metabolic syndrome. Mice deficient of Toll-like receptor 5, a component of the innate immune system that is expressed in the intestinal mucosa, exhibit hyperphagia and develop the hallmark features of metabolic syndrome, including hyperlipidemia, hypertension, insulin resistance, and increased adiposity (Vijay-Kumar, M., et al., Science, 2010. 328(5975):228-31).

Figure 4:
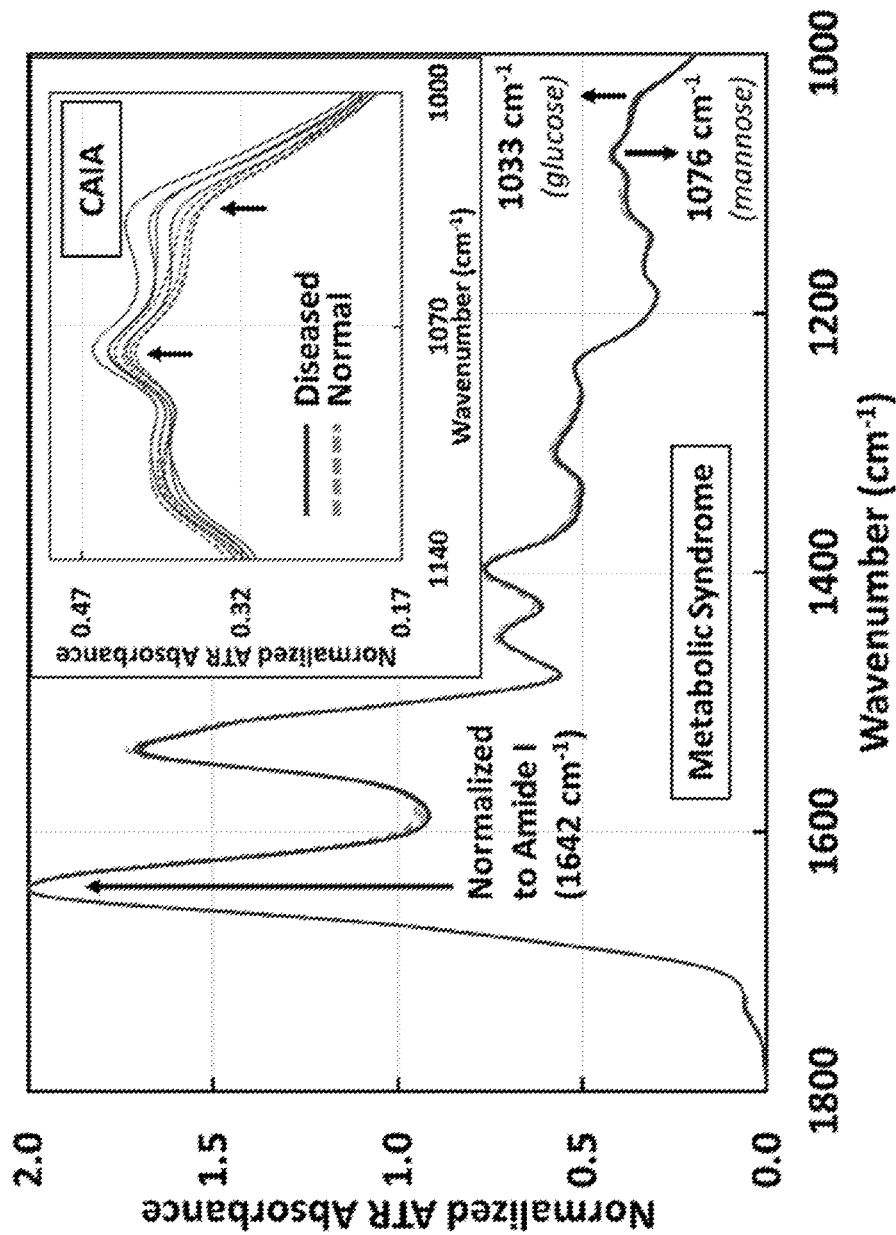
FIG. 4 shows ATR-FTIR spectra of sera drawn from mice before (n=4) and after (n=4) developing metabolic syndrome. In these 8 spectra, the two spectral markers at 1033 cm$^{-1}$ and 1076 cm$^{-1}$ do not show any difference in the metabolic syndrome samples with respect to ATR-FTIR technique. The inset shows the spectra (1140-1000 cm$^{-1}$) of sera drawn from collagen antibody-induced arthritic (n=4) and normal (n=4) mice (total of 8). 1033 cm$^{-1}$ marker is common to colitis and arthritis, but 1076 cm$^{-1}$ marker is unique to colitis. All spectra are normalized to the Amide I peak (1642 cm$^{-1}$).

As seen in FIG. 4, metabolic syndrome samples did not show any significant differences in absorbance at the ~1033 $cm^{-1}$ and ~1076 $cm^{-1}$ peaks with respect to ATR-FTIR spectroscopy in this wavelength range of interest. This indicates that these particular mannose and glucose peaks observed in colitic samples were not a result of metabolic syndrome.

The next objective was to determine whether the absorbance changes in the two peaks at ~1033 $cm^{-1}$ and ~1076 $cm^{-1}$, were specific to intestinal inflammation or associated with any kind of inflammation. Collagen antibody-induced arthritis (CAIA) was employed as a model of extra-intestinal inflammation. An increase in absorbance was seen in arthritic sera samples a ~1033 $cm^{-1}$ (similar to colitic samples), but not at ~1076 $cm^{-1}$ as previously seen in the inset of FIG. 4. This result suggests that the glucose peak might not be specific to colitis but general to an inflammation from any origin. However, the mannose peak at ~1076 $cm^{-1}$ appeared to be specific to colitis. It has been reported that in ulcerative colitis cases in humans, one of the glycoprotein fractions in the colonic mucus has elevated levels of mannose that was confirmed using biological assays (Teague, R., et al. BMJ, 1973. 2(5867):645-646). The lesions on the colon characteristic of colitis can facilitate the diffusion of mannose into the circulating blood stream, thus manifesting as increased levels of mannose in serum. This phenomenon could explain the increased levels of mannose in the colitic mice serum samples in the DSS model at ~1076 $cm^{-1}$ spectral marker. Another study using Proton Nuclear Magnetic Resonance spectroscopy reports that there is a significant increase in mannose levels (Schicho, R., et al., Journal of Proteome Research, 2010. 9(12):6265-6273) in the serum for DSS-induced colitic mice which is confirmed by our ATR-FTIR spectroscopic study.

As seen in FIG. 5A, the absorbance levels at ~1033 $cm^{-1}$ indicated that the glucose peak increased at the onset of arthritis and colitis. The absorbance data points for the metabolic samples did not show a clear separation from the normal in either individual (FIGS. 5A and B) or the average (FIGS. 5C and D) values at ~1033 and ~1076 $cm^{-1}$. The error bars associated with the averaged absorbance values of diseased samples in FIGS. 5c and d were larger than the normal sample values as each mouse could be at a different stage of the disease.

The absorbance data for arthritis also showed a separation at ~1033 $cm^{-1}$ but no appreciable difference in the mannose peak at ~1076 $cm^{-1}$ (FIG. 5B). However, especially for colitis samples, there were clear separations from the normal samples.

Moreover, arthritis serum samples displayed an absorption peak at 1292 $cm^{-1}$ which was observed only for arthritis and not for colitis (both DSS and IL10−/−) or metabolic syndrome serum samples. This peak was identified as thymine (Movasaghi, Z., et al. Applied Spectroscopy Reviews, 2008. 43(2):134-179). It has been reported that, in cases of arthritis, thymidine begins to break down to thymine (Nykänen, P., Scandinavian journal of immunology, 1979. 9(5):477-482) which explains the increased presence of thymine in the serum.

On deconvolution of the spectra by performing the second derivative on the absorbance values (FIG. 6), one can clearly distinguish between the serum samples representative of intra-(colitic) and extra-(arthritic) intestinal inflammation based on the thymine peak.

There was no notable difference in absorbance values for the metabolic syndrome samples and their controls indicating that the presence of metabolic syndrome was not manifested at these spectral markers. The analysis indicated that the increase in glucose peak (1033 $cm^{-1}$) was common to colitis and arthritis, but the increase in mannose peak (1076 $cm^{-1}$) was unique to colitis.

Cluster and heterogeneity analyses, commonly employed in computational biology, were carried out in the spectral range of 1140 to 1000 $cm^{-1}$ to include the glucose (1033 $cm^{-1}$) and mannose (1076 $cm^{-1}$) peaks. The input datasets include the 12 DSS induced colitic and 12 control sample spectra. The resulting data is plotted as a heterogeneity dendrogram chart (FIGS. 7 and 8) indicating that the spectra were correctly grouped together and classified into two clusters, namely control and colitic with a high degree of heterogeniety.

Conclusion

A rapid, simple, cost effective and minimally invasive technique, ATR-FTIR spectroscopy, has been demonstrated as an effective tool to detect colitis in mice serum. The use of a metabolic syndrome mouse model and an arthritis model indicate the specificity of the mannose peak for colitis. A portable device capable of detecting similar variations in mannose and glucose absorbance will require a specific infrared detector capable of simultaneous multiband detection in order to avoid bulky interferometers or gratings. The developments in infrared detector technology allowing room temperature operation of multiband infrared detectors make this possible (Perera, A. G. U., et al., Microelectronics Journal, 2009. 40(3):507-511; Jayaweera, P. V. V., et al. Applied Physics Letters, 2007. 91(6):063114; Ariyawansa, G., et al., Infrared Physics & Technology, 2007. 50(2-3): 156-161; Perera, A., et al., Applied Physics Letters, 2006. 89(13):131118). This technology can be further developed into a personalized diagnostic tool in which patient-to-patient differences in molecular signatures would allow the assessment of disease status and personalized drug management. This technology could be integrated in a portable device, like the current glucometer, that each patient would wear as a platform to monitor multiple health parameters at the point-of-care, facilitating the creation of bedside technologies for diagnostics and treatment monitoring for various other medical conditions (Titus, J., et al., Applied Physics Letters, 2014. 104(24):243705) such as arthritis, viral or bacterial infections, allergies etc including IBD.

Example 2

Screening for Colitis Using (Infrared) Spectroscopic Signatures

Spectroscopic measurements were performed on sera from DSS-induced colitis mice compared to the same mice before intake of DSS (control mice). Spectral deconvolution was performed on the amide I region by taking the second derivative of the absorbance. As seen on FIG. 9, two major peaks (dips in second derivative) are observed at 1635 and 1650 cm$^{-1}$ which are assigned as beta sheet and alpha helix (Movasaghi, Z., et al., Applied Spectroscopy Reviews 2008, 43:134-179) respectively which are components of proteins. The alpha helix to beta sheet ratio is always higher in normal serum samples compared to the DSS induced colitis samples. This can be connected to the selective upregulation/downregulation of certain proteins that are determined as markers (Viennois, E. et al., Journal of proteomics 2015, 112:166-179) for colitis. Arthritis being an extra-intestinal inflammatory model serves as a control for colitis. There is no significant difference in the aforementioned ratios indicating its uniqueness to colitis.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for detecting inflammation in a subject, comprising:
   (a) depositing a bodily fluid sample from the subject on an internal reflection element (IRE);
   (b) directing a beam of infrared (IR) radiation through the IRE under conditions such that the IR radiation interacts with the bodily fluid sample;
   (c) recording an absorption spectrum over a range of preselected frequencies;
   (d) comparing the absorption spectrum to a control spectrum to identify spectral events associated with inflammation; and
   (e) treating the subject for colitis if an increase in the ratio of 1650:1635 cm$^{-1}$ peaks compared to a normal control is detected; or treating the subject for arthritis if peaks are detected at 1033 cm$^{-1}$ but not 1076 cm$^{-1}$; or treating the subject for arthritis if peaks are detected at 1292 cm$^{-1}$.

2. The method of claim 1, wherein the IRE is an attenuated total reflectance (ATR) crystal comprising an optical material with a higher refractive index than the sample.

3. The method of claim 2, wherein the IRE comprises a germanium crystal or a zinc selenide crystal.

4. The method of claim 1, wherein the IR radiation that interacts with the bodily fluid sample is an evanescent wave with an average penetration depth of about 2 μm.

5. The method of claim 1, further comprising Fourier transformation of the absorbance spectrum.

6. The method of claim 1, wherein the range of preselected frequencies is between 50 cm$^{-1}$ and 3700 cm$^{-1}$.

7. The method of claim 1, wherein the bodily fluid sample comprises a blood, serum, or plasma sample.

* * * * *